United States Patent

Hartmann et al.

(10) Patent No.: US 6,591,226 B1
(45) Date of Patent: Jul. 8, 2003

(54) ACOUSTIC DIAGNOSTIC SYSTEM AND ASSOCIATED METHOD

(75) Inventors: Doris Hartmann, Gundelsheim (DE); Sofiane Kacem, Nuremberg (DE); Karl-Heinz Maier, Nuremberg (DE); Nicolai Plewinski, Roethenbach/Pegnitz (DE); Thomas Voelkel, Bad Steben (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/688,801

(22) Filed: Oct. 17, 2000

Related U.S. Application Data

(63) Continuation of application No. PCT/DE99/01118, filed on Apr. 14, 1999.

(30) Foreign Application Priority Data

Apr. 17, 1998 (DE) .......................................... 198 17 169

(51) Int. Cl.⁷ .......................... G06F 19/00; G06F 11/30
(52) U.S. Cl. .......................................... 702/183; 702/56
(58) Field of Search ................................ 702/183, 182, 702/184, 185, 56, 33, 34, 35, 84; 73/587, 570, 602

(56) References Cited

U.S. PATENT DOCUMENTS

| | | | | |
|---|---|---|---|---|
| 5,305,235 A | * | 4/1994 | Izui et al. ............... | 364/551.01 |
| 5,333,240 A | * | 7/1994 | Matsumoto et al. ......... | 395/23 |
| 5,511,004 A | | 4/1996 | Dubost et al. | |
| 5,511,422 A | * | 4/1996 | Hernandez .................... | 73/593 |
| 5,566,092 A | * | 10/1996 | Wang et al. ............ | 364/551.02 |
| 5,602,757 A | * | 2/1997 | Haseley et al. ......... | 364/551.01 |
| 5,602,761 A | * | 2/1997 | Spoerre et al. .............. | 364/554 |
| 5,710,723 A | * | 1/1998 | Hoth et al. ............ | 364/551.01 |
| 5,761,090 A | * | 6/1998 | Gross et al. ........... | 364/551.01 |
| 5,852,793 A | * | 12/1998 | Board et al. .................. | 702/56 |
| 5,943,634 A | * | 8/1999 | Piety et al. .................... | 702/56 |
| 5,963,884 A | * | 10/1999 | Billington et al. ............ | 702/56 |
| 5,991,707 A | * | 11/1999 | Searles et al. ............... | 702/185 |
| 5,995,910 A | * | 11/1999 | Discenzo ..................... | 702/56 |
| 6,041,287 A | * | 3/2000 | Dister et al. ................. | 702/182 |
| 6,192,325 B1 | * | 2/2001 | Piety et al. .................. | 702/184 |
| 6,199,018 B1 | * | 3/2001 | Quist et al. .................... | 702/34 |
| 6,256,594 B1 | * | 7/2001 | Yamamoto et al. ......... | 702/185 |

FOREIGN PATENT DOCUMENTS

| | | |
|---|---|---|
| DE | 42 07 728 A1 | 9/1993 |
| WO | WO 98/01728 | 1/1998 |

* cited by examiner

*Primary Examiner*—Patrick Assouad
(74) *Attorney, Agent, or Firm*—Sughrue Mion, PLLC

(57) ABSTRACT

The invention relates to an acoustic diagnostic system and an associated method, wherein the system includes a sensor mechanism to convert mechanical vibrations into electrical signals. The acoustic diagnostic system furthermore includes a signal conditioning unit to amplify and low-pass filter the electrical signals and an analog/digital converter to convert the amplified and low-pass filtered signals into discrete digital data. In addition, a signal processing unit, which performs signal analysis, extraction of characteristics, and classification of error classes and/or quality classes, which are associated with a respective test object of the digital data, is provided. Finally, the acoustic diagnostic system includes an archive to automatically archive an occurrence and a frequency of the error classes and/or the quality classes. The diagnostic system preferably includes controlling means that control the production process for the manufacture of the test object.

22 Claims, 6 Drawing Sheets

ACOUSTIC DIAGNOSTIC SYSTEM AND ASSOCIATED METHOD

This is a Continuation of International Application PCT/DE99/01118, with an international filing date of Apr. 14, 1999, the disclosure of which is incorporated into this application by reference.

FIELD OF AND BACKGROUND OF THE INVENTION

The present invention relates to an acoustic diagnostic system and an associated method, which are particularly suitable for an automatic quality control of test objects, such as motors or ceramics.

Such a testing system and testing method are used, for instance, to detect and evaluate signals. Therein, a combination of measuring hardware and signal processing software is often used. This often requires the knowledge and experience of an expert, due to the complexity of such a measurement arrangement.

WO 98/01728 discloses a device to detect analog measurement signals to acoustically diagnose test objects. Vibration sensors are used to detect analog measurement signals from a test object. A computer is equipped with a standard interface card to digitize the measurement signals. A switching signal generates a trigger signal, which can be input via an interface. This interface is preferably a serial interface. Via the trigger signal, a control program in the computer switches the input of the measurement signals on and off.

OBJECTS OF THE INVENTION

It is one object of the invention to provide an acoustic diagnostic system and an associated method, which enables automatic quality control in a simple manner.

SUMMARY OF THE INVENTION

According to one formulation of the invention, this and other objects of the invention are achieved an acoustic diagnostic system, which includes a sensor mechanism to convert mechanical vibrations into electrical signals. The acoustic diagnostic system furthermore includes a signal conditioning unit to amplify and low-pass filter the electrical signals and an analog/digital converter to convert the amplified and low-pass filtered signals into discrete digital data. In addition, a signal processing unit for signal analysis, for extraction of characteristics, and for classification of error classes and/or quality classes, which are associated with a respective test object is provided. Finally, the acoustic diagnostic system includes an archive to automatically archive an occurrence and a frequency of the error classes and/or the quality classes.

According to another formulation of the invention, this and other objects are achieved by a method to control the quality of a test object, which includes the steps of converting mechanical vibrations into electrical signals; amplifying and low-pass filtering the electrical signals; converting the amplified and low-pass filtered signals into discrete digital data; analyzing the signals; extracting characteristics; classifying error classes and/or quality classes, which are associated with the respective test object; and automatically archiving the occurrence and the frequency of the error classes and/or the quality classes.

Due to the acoustic diagnosis, the diagnostic system enables an automatic and straight-forward, verifiable quality control, in particular in the manufacturing process of products, for which an acoustic diagnosis permits conclusions as to the quality of the products.

Contrary to previous acoustic tests, which must often be performed by specialists, the diagnostic system according to the invention can be used as often as desired. Additionally, the automatic archiving of the quality tests allows for reliable and straight-forward, verifiable reexamination at any time.

The integration of the diagnostic system into a production process is performed in that the diagnostic system includes a controller, or in that it is connected to a controller, which control of the production process of test objects.

A descriptive classification of test objects is ensured in one of two ways. As a first alternative, the diagnostic system includes a component, which, based on an input signal, determines several classifications. As a second alternative, the diagnostic system includes a component, which based on an input signal that is assigned to the test object, determines several characteristics for the classification of the test object. Therein, the characteristics or features assigned to each class are color-coded.

An optimized determination of the number of features is ensured in that the diagnostic system includes a component to determine redundant features, which, in turn, determine a correlation of existing features.

A capability to filter redundant features is provided by means of the diagnostic system for creating a correlation matrix to visualize redundant features.

Advantageous applications of the diagnostic system are found in quality control, in particular in the quality control of self-energized test objects, such as motors, and/or in the quality control of separately energized test objects, such as glass or ceramics.

BRIEF DESCRIPTION OF THE DRAWINGS

The invention and further advantageous refinements of the invention according to the features of the dependent claims are explained in more detail below with the aid of diagrammatic, exemplary embodiments in the drawings. The drawings show:

DETAILED DESCRIPTION OF THE PREFERRED EMBODIMENTS

Figure 1:
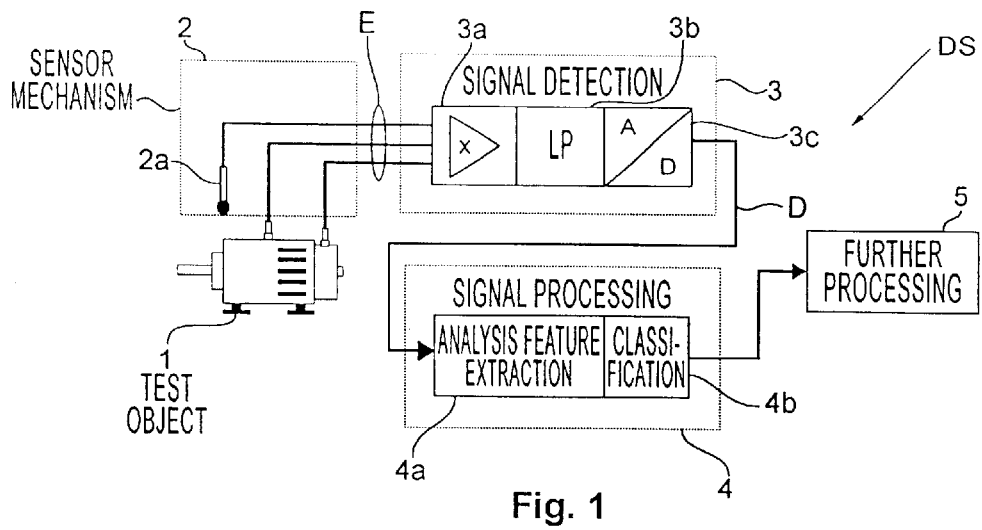
FIG. 1 a principle illustration of an acoustic diagnostic system.

FIG. 1 shows a principle illustration of an embodiment of an acoustic diagnostic system for diagnosing a test object 1, the quality and/or function of which is to be determined.

The test object 1 of the embodiment in FIG. 1 is, for example, an electric motor. The electric motor is a self-energized test object, which, in an operation mode, vibrates on its own. Alternatively, separately energized test objects, such as ceramics, glass, etc., can be tested with the diagnostic system illustrated in FIG. 1. By an external pulse, these separately energized test objects must be energized or excited into vibration. A signal detection is broken down into several levels. A sensor mechanism 2 is arranged at the beginning of the processing chain. The sensor mechanism 2 converts of mechanical magnitudes or measurands, which represent a vibration, into electric signals. A variety of magnitudes includes a vibration path s, speed v, and acceleration a. From this variety of magnitudes, it is often the acceleration a that is detected. The acceleration (body sound signal or object sound signal or structure-borne signal) is detected by piezoelectric acceleration sensors, which are directly attached the test object. To determine an airborne noise level, microphones 2a are used, which are arranged in the immediate vicinity of the test object. The next level is represented by a signal conditioning 3. Electronic signals E, which are emitted by the sensors, are amplified and low-pass filtered in a low-pass filter 3b (Aliasing). Finally, an A/D converter 3c converts the analog measurands into discrete digital values D for subsequent computer-aided evaluation. Signal processing 4 includes a signal analysis/feature extraction 4a and a classification 4b.

The signal analysis 4a extracts characteristic results from the detected and converted signals—the so-called features or characteristics—by means of which the signals are described. The purpose of the analysis is a data reduction of the measurement values, without losing relevant information on the test object. The most commonly used analysis method in vibration analysis is the Fast Fourier Transformation (FFT). Therein, the time signal is transformed into the frequency components the time signal is composed of. The results of the different analysis methods are components of the feature-extraction.

Characteristic features are defined, with which a quality class of the test object is determined. During the classification process, an assignment of the test object to individual quality classes is performed. The classification can be based on simple thresholds; however, complex algorithms (neuronal nets, fuzzy logic, cluster analysis, etc.) may also be used.

The result of the classification can also serve to control a production process 5. For example, a defective part is precluded from the process for subsequent postprocessing. In addition, data on the occurrence and frequency of error classes are archived. Thereby, conclusions for the production process can be drawn. For example, increased occurrence of bearing damages in electric motors might indicate that a different type of bearing should be used. It can be recognized that technical knowledge from the fields of vibration acoustics, measurement technology, and data processing, and technical knowledge on the technology of the test object is required to develop and parameterize the individual components of a test system.

The automated diagnostic system shown in FIG. 1 meets increasing quality requirements of the production process. Due to the automation of the diagnostic system, the diagnostic system functions with uniform precision and in accordance with objective criteria. In addition, it also meets the requirements of low production costs and high productivity rate. To be able to draw conclusions about the production process, the test system is capable of assigning the quality classes or error classes of a product to a respective production stage. Therein, the selection of the diagnostic signal, from which information about the test object is to be obtained, plays a critical role. With the aid of the sensor mechanism shown in FIG. 2, the diagnostic signal is easily detected and can be evaluated within the respective production stage. In addition to the vibration behavior of the test object, i.e., the vibration of the test object 1, not only this, but also the resultant noise can be considered. Furthermore, the diagnostic system shown in FIG. 1 can also be parameterized by a user in a simple way.

Figure 2:
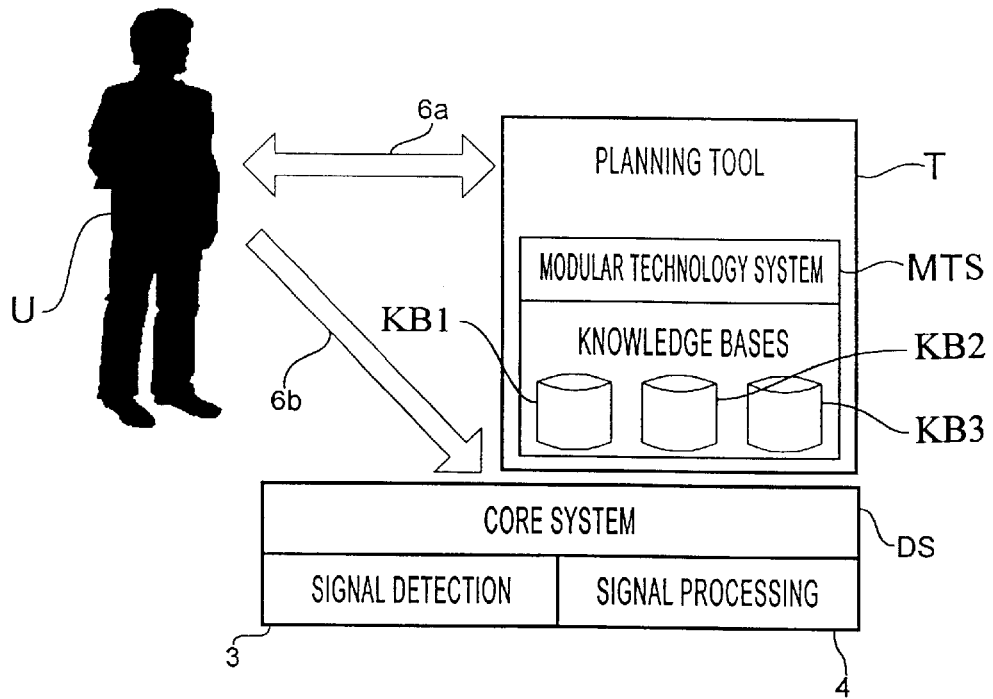
FIG. 2 a principle illustration of fundamental components of an intelligent acoustic diagnostic system.

FIG. 2 shows an exemplary representation of the principle of the fundamental components of an intelligent acoustic diagnostic system DS having an associated planning tool PT. The diagnostic system DS includes the components already described in FIG. 1: the signal detection 3 and the signal processing 4. The planning tool PT includes a modular technology system MTS having knowledge bases KB1 . . . KB3. The diagnostic system DS and the planning tool PT are accessed by the user via user interfaces 6a and 6b.

To obtain the desired evaluation of the test object 1, the components of the diagnostic system must be appropriately parameterized and matched with each other. The systems currently on the market are systems that have been developed and assembled by experts from various fields. This results in high planning expenditure. This high planning expenditure is incurred for each new type of test object. Standard methods, which are adjusted to the testing task at hand, are used in individual steps. The adjustment is made on the basis of expert knowledge. The knowledge from the various fields makes it practically impossible for a single person to configure a complete system on his or her own. This leads to the need for developing a universal test system, which supports the user in the planning phase by means of a knowledge base regarding the technology of the object to be tested and regarding the relevant measurement and evaluation methodology. Thereby, the planning expenditure is reduced.

The diagnostic system DS shown in FIGS. 1 and 2 can be easily adapted to the most various testing tasks in vibroacoustic diagnosis. In addition, the user is supported by the system during the planning phase and parameterization phase in the form of proposals. Furthermore, the user is guided in the logical procedure. Therein, it is necessary to divide the system into a generally usable core and industry-specific supplements. An industry-specific supplement is called a modular technology system MTS, to which the planning tool is added. The core system can also be planned without support from the modular technology system MTS. In this case, however, a high degree of knowledge about the processes used is expected from the user U.

Figure 3:
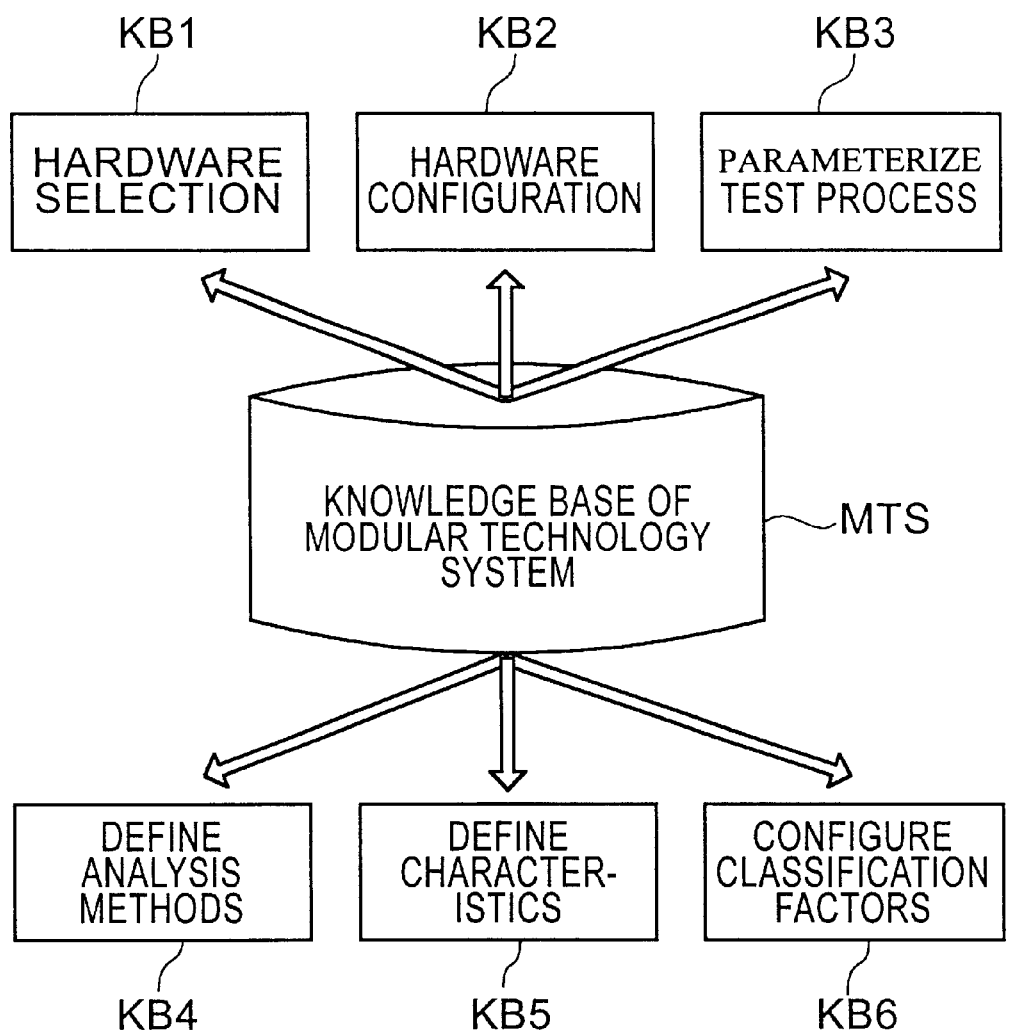
FIG. 3 a schematic illustration of exemplary tasks of knowledge bases of a modular technology system.

FIG. 3 shows a schematic representation of exemplary tasks of the knowledge bases KB1 . . . KB6 of a modular technology system MTS.

There are a number of requirements for the modular technology system MTS in order to parameterize the diagnostic system with the support of an assistant. A modular technology system includes the knowledge bases KB1 . . . KB6, which include information about the technology of the test object, about the associated vibro-acoustic characteristics, about measurement-technological interrelations, and about the signal-processing methodology. This information and the rules derived therefrom support the user, as shown in FIG. 3, in configuring the system.

The modular technology system must also be capable of supporting the user in the following tasks:
 selection of test means;
 test conditions; and
 signal evaluation.

Selecting the test means involves proposing to an operator suitable sensors and appropriate detection hardware for his testing task from a known hardware catalog. An additional aspect is the support during configuration of the selected hardware components, e.g., at which position and with which process a sensor is to be arranged.

The determination of the test conditions, under which the test object is to be detected, requires the support of the modular technology system. Therein, the test conditions affect the test object directly and indirectly. An example of a direct test condition is the type of stimulation or excitation of a ceramic test object. A maximum permissible sound level in the environment is an example for an indirect test condition.

Another task, in which the planner is to be supported, is the selection of appropriate signal-processing methods. The selection of the appropriate signal-processing methods starts with a selection and parameterization of an analysis method, with which the obtained signals are to be processed. Likewise, the interpretation of the analysis result from a technical viewpoint requires knowledge about the technical knowledge of the modular technology system MTS. With the aid of these interpretations and with the aid of the technological knowledge of the modular technology system, the user defines meaningful characteristics. Similar to the analysis method, the knowledge of the modular technology system regarding the methodology is employed.

In order to provide the support for the operator, information about the test object must be supplied to the modular technology system in advance of the actual planning phase. The modular technology system receives this information from the user, who asks the operator questions about the relevant properties of the test object.

To include additional types of test objects in the modular technology system MTS, the MTS must be structured in such a way that this inclusion is easily accomplished and that this inclusion builds upon knowledge that already exists in the MTS. The user must be able to add his individual knowledge to the modular technology system. The flexibility of the modular technology system is an important aspect. This aspect governs the structure of the MTS. Still, the structure of the various modular technology systems must be uniform, so that the basic system operates independently of the type of modular technology system MTS. These requirements for the modular technology system MTS and its knowledge base are implementation requirements.

Figure 4:
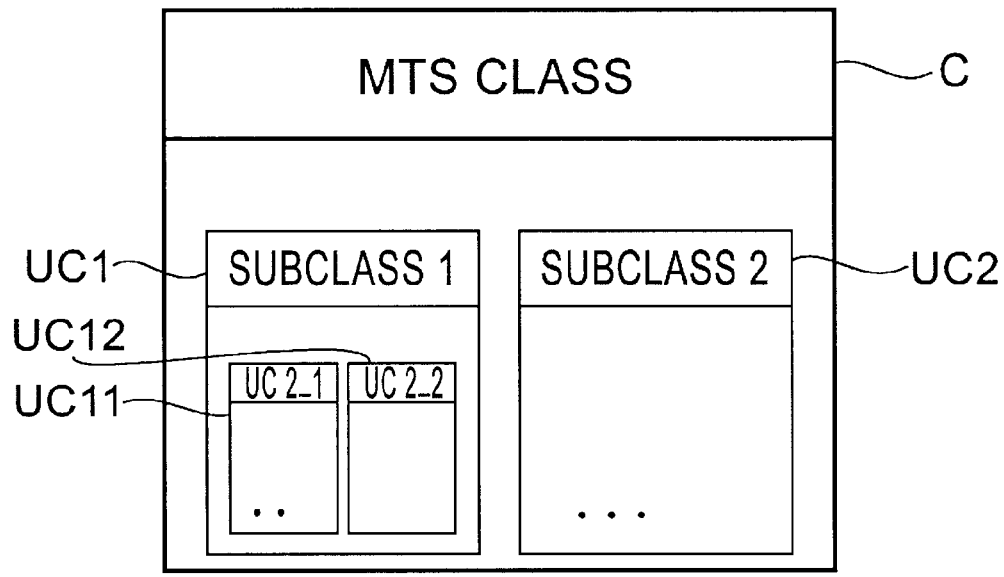
FIG. 4 an exemplary structure of a modular technology system.

FIG. 4 shows an exemplary structure of a modular technology system MTS. The modular technology system MTS includes a class C and subclasses UC1, UC2, each of which, in turn, can be built on subordinate components UC11, UC12.

Thereby, the requirements for flexibility and expandability are met. A class C includes knowledge in the form of rules and functions that use and interpret these rules. In this class structure, parallels can be drawn to the structure of object-oriented programming. Each subclass UC specifies more precisely the knowledge and the functionality of its subordinate classes. Thus, a superior class "rotating machines" (e.g. rotational speed information) is specified more precisely by a subclass "electric motor" (e.g. information about the number of poles, etc.). Such classes can be specified even further through additional subclasses (e.g. an additional class "asynchronous motors").

Such a structure of the modular technology systems is capable of generating logically reasonable modular technology systems from various modular systems. Therein, fairly complex modular systems can be generated without high expenditure; it suffices to add specific characteristics.

Figure 5:
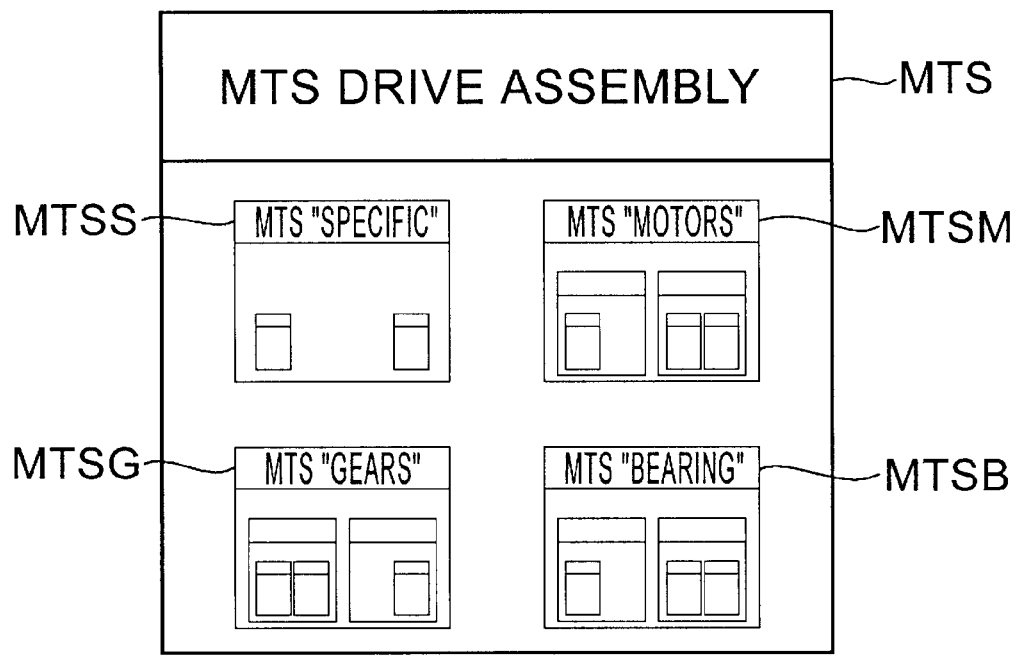
FIG. 5 an exemplary structure of an assembled modular technology system "drive assembly"

FIG. 5 shows the so-obtained structure MTS of an assembled modular technology system "drive assembly". As an example, the modular technology system "drive assembly" includes parts from the modular technology systems MTSM "motors", MTSB "bearings", and MTSG "gears". In addition, the modular technology system MTSs "specific knowledge" on the behavior of a drive assembly and on additionally required functionality are parts of the MTS "drive assembly".

The structure of a knowledge basis for implementing an MTS includes essentially the following sections:

1. General overview of the specific industry and introduction into the fundamentals of that specific industry;
2. Division into parts in accordance with vibro-acoustic aspects; attempt to describing the vibration behavior;
3. Lab measurements of selected collective data or universes;
4. Analysis of lab tests; and
5. Verification and specification of knowledge In the first step, an overview of the product diversity of the respective industry is obtained, for which the modular technology system MTS is to be developed. Therein, a broad framework is set with regard to the specific product fields to be covered by the modular technology system MTS. In addition, from a vibro-acoustic standpoint, the user familiarizes himself or herself with the technological basics of the respective field in order to interpret the behavior observed. The next step includes the structuring of the industry into individual subclasses, which have similar technological properties and, thus, a similar vibration behavior and sound behavior.

Before collective data or universes are tested in the lab, attempts are made to describe the test object based on its technological data reflecting its vibration behavior. Therein, one learns which technological data are of relevance for the modular technology system MTS, and, thus, which technological data have to be inquired about by the user prior to the actual parameterization of the testing system. Upon completion of the theoretical considerations, typical representatives of the subdivided classes are selected. These representatives are tested in the lab. The lab tests clarify which measuring means and which measuring methods are most suitable to detect various vibro-acoustic phenomena. Also, the tests determine which non-vibration magnitudes or measurands may have to be detected in order to allow for a subsequent evaluation, for example. In the case of a modular technology system MTS for "glass", the environmental temperature may be such a measurand, for example.

The measuring data are then subjected to various analysis methods in order to find out which method and which parameters are most suitable for the particular test object. In addition, it is examined how a vibration phenomenon is reflected in the analysis result and what the underlying technical aspect for the vibration phenomenon is. Furthermore, it is determined which vibration phenomena are of general nature. Only knowledge that can be transferred to other types of test objects, is added to the knowledge base. Later, this knowledge supports the user in interpreting his measurement results. Support in defining the characteristics can only be accomplished if generally valid characteristics for certain error classes can be diagnosed.

The last step summarizes the knowledge acquired during the previous steps. A comparison is performed to find out which model forecasts were confirmed in the lab tests and which model forecasts must be modified or even discarded.

Once a solid knowledge basis is obtained in this manner, this knowledge is incorporated into the structure of the modular technology system MTS. The described sequence can be performed successively, i.e. an existing modular technology system MTS can be expanded by new types of test objects in a step-by-step manner.

Figure 6:
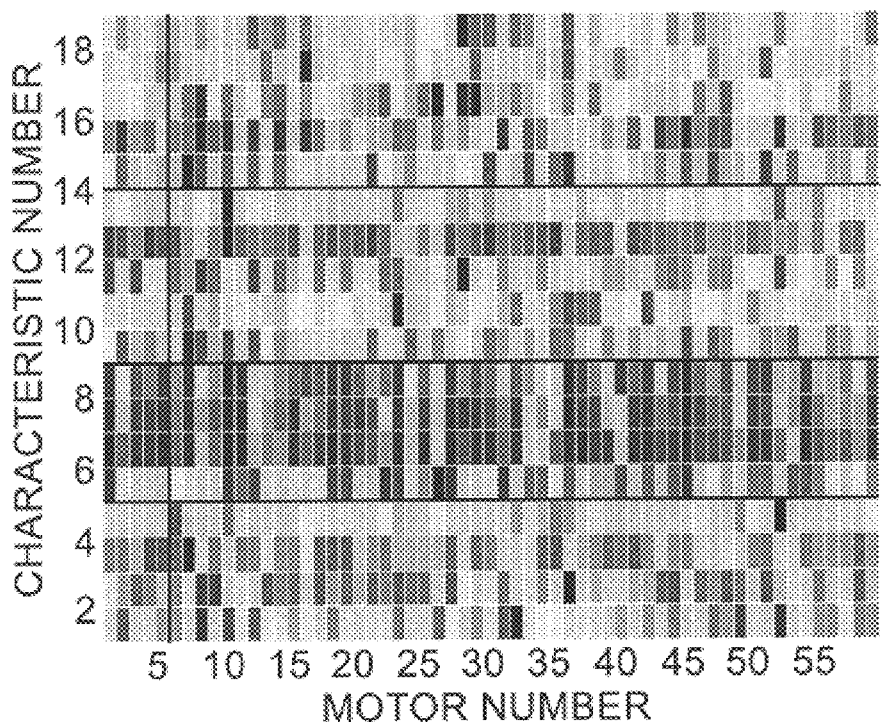
FIG. 6 an exemplary illustration of a feature evaluation or characteristics evaluation.

FIG. 6 shows an example of a characteristics evaluation for 18 characteristics and 59 motors, which were the test objects. The classification of the motors into respective classes s on the basis of one characteristic describes the motor's quality. In order to get an overall impression of the effectiveness of the characteristics, all 18 characteristics of each motor are shown by way of missing color plots. Each line of characteristics was standardized according to its maximum value. The value of a characteristic is coded by a color (the color range runs from blue (0) through green/yellow (0.5) to red/brown (1)).

The classifications in FIG. 6 show motors classified as good motors (numbers 1 to 5) and motors classified as bad motors (numbers 6 to 59) (vertical line). In addition, FIG. 6 shows various channels (horizontal lines: housing radial 1–4; housing tangential 5–8; bearing A 9–13 and bearing B 14–18).

The ideal case is a uniform color tone per characteristic of the first five motors, from which color tone the remaining ones differ. Those characteristics are then especially well-suited for a classification on the basis thresholds. If the color tones of the good and bad motors match, then this match indicates an insignificant characteristic.

Figure 7:
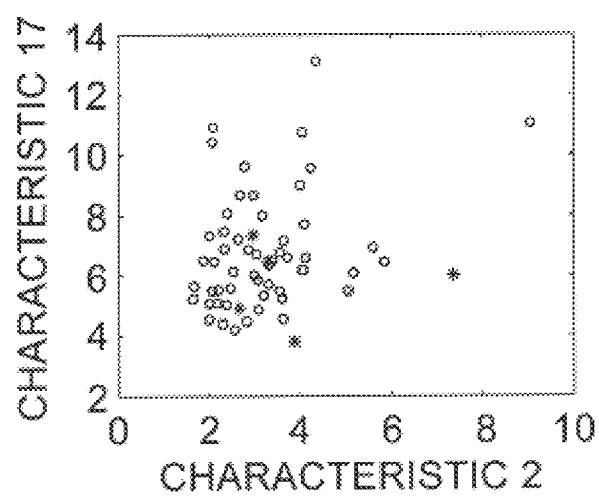
FIGS. 7–9 respective illustrations for individual characteristics in the form of scatter plots.
Figure 8:
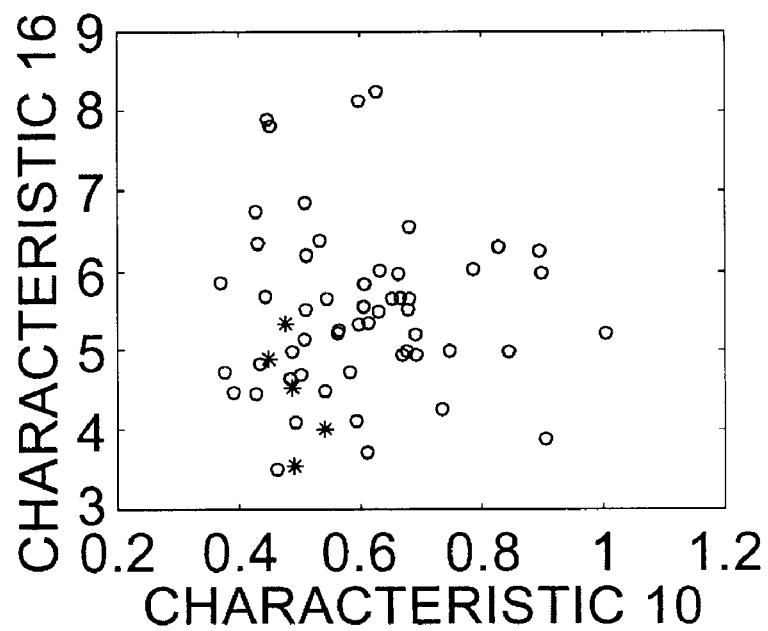
Figure 9:
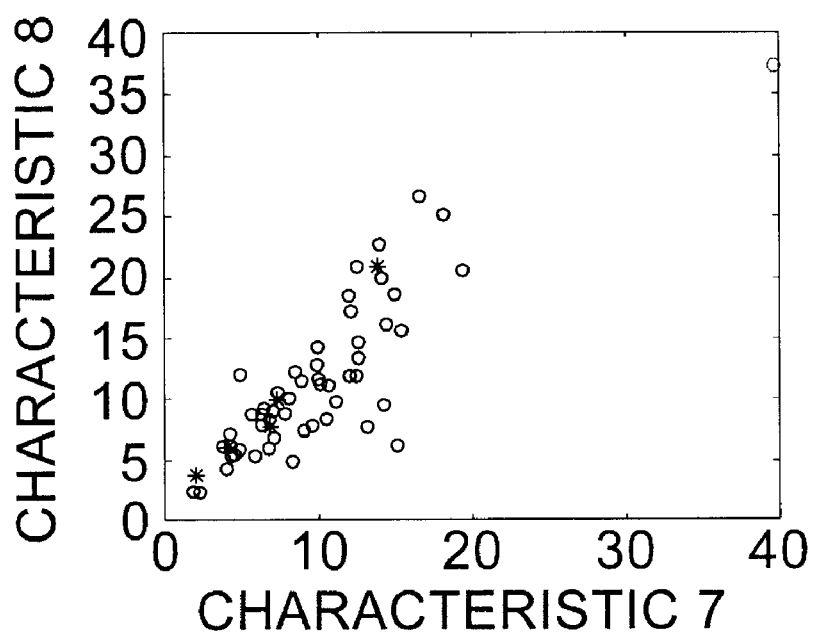

Based on such a representation, scatter plots were drawn for the various characteristics. Three of those plots are shown in FIG. 7 to FIG. 9. The good motors are identified by green stars, whereas the bad ones are identified by red circles.

FIG. 7. shows the characteristics 2 (housing radial 3fL–SfL) and 17 (bearing B plain bearing vibrations). As shown, the two characteristics do not provide a good differentiation between the motors. This can also be learned from FIG. 6. A better differentiation of the motors is provided by the two characteristics 10 (bearing A lamellar frequency) and 16 (bearing B 5fL–9fL) (illustration 4–18). About 40 out of the 54 defective motors can be differentiated by choosing a threshold for each characteristic. This is also shown in FIG. 6 where the characteristics 10 and 16 of the first five motors show a uniform color tone, whereas the bad motors show color tones of higher intensity.

In the ideal case, if distinguishability of two characteristics is provided, a cluster of good motors would be present, which does not intersect with the ones of the other error classes. However, it is likely that several characteristics are always needed in order to properly classify all motors. In illustration 4–19, characteristics 7 and 8. Interestingly enough, all dots are positioned on a diagonal line. This structure indicates that both characteristics are statistically dependent on each other. Thus, both characteristics provide the same information.

The next paragraph describes in more detail how to identify redundant characteristics via the correlation of characteristics: In selecting characteristics, redundant characteristics are filtered out. Redundant characteristics are identified by their feature of showing the same behavior as other characteristics. In order to identify such characteristics, it is useful to employ the correlation function. The result of this method function yields a correlation coefficient between 0 and 1. A correlation coefficient of "1" means that the characteristics are statistically dependent on each other, while a correlation coefficient of "0" implies that they are not.

In order to calculate the correlation coefficients, three times ten data per characteristic resulting from reproducibility measurements were used.

Figure 10:
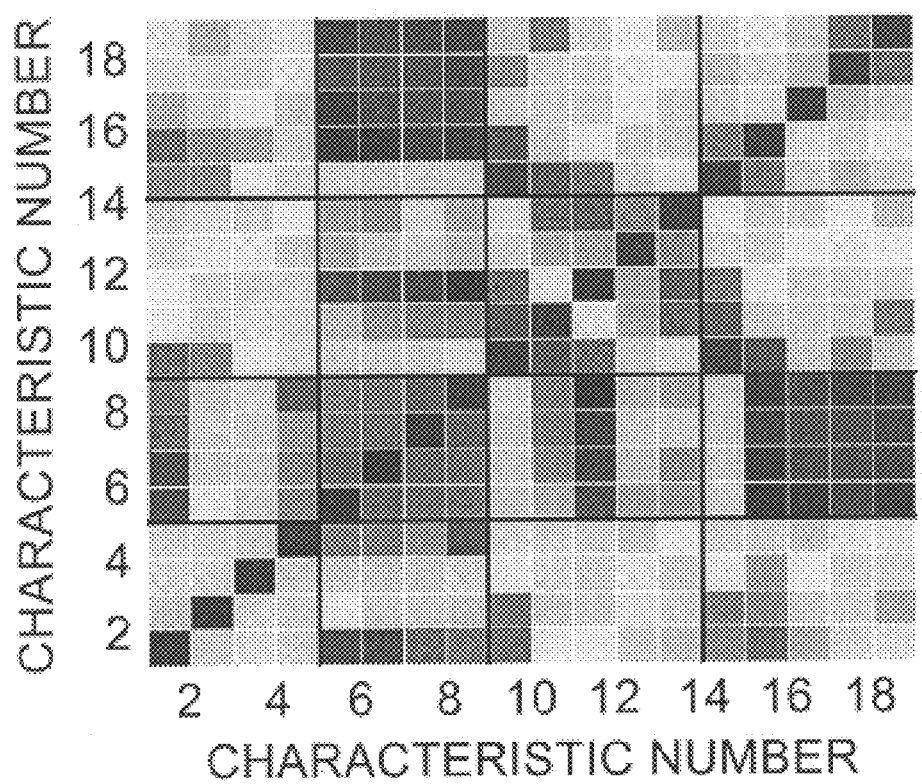
FIG. 10 an exemplary correlation matrix.

FIG. 10 shows the calculated correlation matrix of the 18 characteristics (colors running from blue (0) to red/brown (1)). The characteristics are subdivided into four receiving channels (housing radial 1–4; housing tangential 5–8; bearing A 9–13; bearing B 14–18). It is quite obvious that the characteristics five through eight are strongly correlated with each other (red-brownish shade), while they show hardly any similarities with the other characteristics. This is not surprising as those are "tangential" characteristics, whereas for the remaining characteristics radial vibrations were used. It can also be seen that characteristics, which are based on the same technological concepts (characteristic 9/14 $f_O$ and characteristic 1/15 $f_L$); show a similar pattern. This is also true for the characteristics 12/13 and 17/18, which evaluate the upper frequency area of the bearing vibrations. In combination with the quality of the characteristics, this method provides a good opportunity to identify redundant characteristics. This method can also be used to minimize the number of sensor. This is possible when the relevant characteristics of one channel are reflected in characteristics of other channels.

In summary, the present invention is related to an acoustic diagnostic system and an associated method, wherein the system includes a sensor mechanism to convert mechanical vibrations into electrical signals. The acoustic diagnostic system furthermore includes a signal conditioning unit to amplify and low-pass filter the electrical signals and an analog/digital converter to convert the amplified and low-pass filtered signals into discrete digital data. In addition, a signal processing unit for signal analysis, for extraction of characteristics, and for classification of error classes and/or quality classes, which are associated with a respective test object is provided. Finally, the acoustic diagnostic system includes an archive to automatically archive an occurrence and a frequency of the error classes and/or the quality classes. The diagnostic system is preferably includes controlling means that control the production process for the manufacture of test object 1.

The above description of the preferred embodiments has been given by way of example. From the disclosure given, those skilled in the art will not only understand the present invention and its attendant advantages, but will also find apparent various changes and modifications to the structures and methods disclosed. It is sought, therefore, to cover all such changes and modifications as fall within the spirit and scope of the invention, as defined by the appended claims, and equivalents thereof.

What is claimed is:

1. An acoustic diagnostic system, comprising:

a sensor mechanism to convert mechanical vibrations of a test object into electrical signals;

a signal conditioning unit to amplify and low-pass filter the electrical signals;

an analog/digital converter to convert the amplified and low-pass filtered signals into discrete digital data;

a signal processing unit to perform a signal analysis, an extraction of characteristics of the electrical signals, and a classification of the characteristics into an error class of mechanical defects in the physical structure of the test object and a quality class indicative of an overall quality of the test object;

an archive to automatically archive an occurrence of the error class and the quality class, and to automatically archive a frequency of occurrences of the error class and the quality class; and a component to detect redundant ones of the characteristics by determining correlations between the characteristics.

2. The diagnostic system of claim 1, wherein the diagnostic system is configured for an automatic quality control of the test object.

3. The diagnostic system of claim 1, wherein the test object is selected from the group consisting of motors and ceramics.

4. The diagnostic system of claim 1, wherein the sensor mechanism comprises at least one sound sensor.

5. The diagnostic system of claim 1, further comprising a controller to control a process for a production of the test object.

6. The diagnostic system of claim 1, wherein the signal processing unit comprises a component to determine classifications based on an input signal of the test object.

7. The diagnostic system of claim 1, wherein the signal processing unit comprises a component to determine characteristics to classify the test object, wherein the component determines the characteristics based on an input signal assigned to the test object, wherein the characteristics are associated with respective classes, and wherein the associated characteristics are color-coded.

8. The diagnostic system of claim 1, wherein the component generates a correlation matrix in order to visualize redundant characteristics.

9. The diagnostic system of claim 1, wherein the diagnostic system is configured for a quality control of at least one of a self-energizing test object and a separately energized test object.

10. The diagnostic system of claim 9, wherein the self-energizing test object is a motor, and wherein the separately energized test object is selected from the group consisting of glass and ceramics.

11. A system, comprising:
   an acoustic diagnostic component, comprising:
      a sensor mechanism to convert mechanical vibrations of the test object into electrical signals;
      a signal conditioning unit to amplify and low-pass filter the electrical signals;
      an analog/digital converter to convert the amplified and low-pass filtered signals into discrete digital data;
      a signal processing unit to perform a signal analysis, an extraction of characteristics of the electrical signals, and a classification of the characteristics into an error class of mechanical defects in the physical structure of the test object and a quality class indicative of an overall quality of the test object; and
      an archive to automatically archive an occurrence of the error class and the quality class, and to automatically archive a frequency of occurrences of the error class and the quality class;
   a planning tool comprising a component that detects redundant ones of the characteristics by determining correlations between the characteristics; and
   a controller to control a production process utilizing the test object.

12. A method for a quality control of a test object, comprising:
   (a) converting mechanical vibrations into electrical signals;
   (b) amplifying and low-pass filtering the electrical signals;
   (c) converting the amplified and low-pass filtered signals into discrete digital data;
   (d) analyzing the digital data;
   (e) extracting characteristics of the electrical signals based on the digital data;
   (f) classifying the characteristics into an error class of mechanical defects in the physical structure of the test object and a quality class indicative of an overall quality of the test object;
   (g) automatically archiving an occurrence of the error class and the quality class;
   (h) automatically archiving a frequency of occurrences of the error class and the quality class; and
   (i) identifying redundant ones of the characteristics by determining correlations between the characteristics.

13. The method of claim 12, wherein the quality control of the test object is an automatic quality control.

14. The method of claim 12, further comprising controlling a process for production of the test object.

15. The method of claim 12, wherein, in the classifying step, classifications are determined based on an input signal of the test object.

16. The method of claim 12, wherein, in the classifying step, characteristics to classify the test object are determined; wherein, in the classifying step, the characteristics are determined based on an input signal assigned to the test object; and wherein, in the classifying step, the characteristics are associated with respective classes; and wherein the associated characteristics are color-coded.

17. The method of claim 13, wherein the identifying step comprises generating a correlation matrix of the characteristics.

18. The method of claim 12, wherein the method controls a quality of at least one of an self-energizing test object and a separately energized test object.

19. The method of claim 18, wherein the self-energizing test object is a motor, and wherein the separately energized test object is selected from the group consisting of glass and ceramics.

20. An apparatus, comprising:
   a sensor mechanism converting mechanical vibrations of test objects into electrical signals;
   a signal conditioning unit conditioning the electrical signals into conditioned digital data;
   a signal processing unit extracting characteristics from the digital data, and classifying the extracted characteristics into error classes of mechanical defects in the physical structure of the test objects and quality classes indicative of respective overall quality of the test objects; and
   a planning tool utilized to detect ones of the characteristics that are redundant.

21. The apparatus according to claim 20, wherein the planning tool comprises a component displaying a matrix correlating the characteristics.

22. A method, comprising:
   converting mechanical vibrations of test objects into electrical signals;
   conditioning the electrical signals into conditioned digital data;
   extracting characteristics from the digital data;
   classifying the characteristics into error classes of defects in the test objects and quality classes indicative of quality of the test objects; and
   utilizing correlations among the characteristics to filter redundant ones of the characteristics.

* * * * *